United States Patent [19]

Sakurai et al.

[11] Patent Number: 4,574,627
[45] Date of Patent: Mar. 11, 1986

[54] AIR-FUEL RATIO DETECTOR AND METHOD OF MEASURING AIR-FUEL RATIO

[75] Inventors: Shigenori Sakurai; Takashi Kamo; Tadayoshi Ikai, all of Aichi, Japan

[73] Assignee: Toyota Jidosha Kabushiki Kaisha, Toyota, Japan

[21] Appl. No.: 576,957

[22] Filed: Feb. 3, 1984

[30] Foreign Application Priority Data

Jul. 20, 1983 [JP] Japan .................. 58-132476

[51] Int. Cl.$^4$ .......................... G01M 15/00
[52] U.S. Cl. ........................ 73/116; 73/23; 204/412; 204/426
[58] Field of Search ............ 73/23, 116; 123/489; 204/412, 426, 421, 422, 423, 424, 425, 427, 428, 429

[56] References Cited

U.S. PATENT DOCUMENTS 4,264,425  4/1981  Kimura et al. .............. 204/425 X
4,498,968  2/1985  Yamada et al. .............. 204/426 X Primary Examiner—Jerry W. Myracle
Attorney, Agent, or Firm—Oblon, Fisher, Spivak, McClelland & Maier

[57] ABSTRACT

An air-fuel ratio detector and an air-fuel ratio measuring method for detecting an oxygen density in an exhaust gas emitted from the internal combustion engine of an automobile. The air-fuel ratio detector has a tubular body and a pair of partition members dividing the tubular body into a closed-end section and an open-end section. At least one of the partition members comprises a solid electrolyte permeable to oxygen ions. A pair of electrodes is mounted on opposite surfaces of the solid electrolyte and connected to a DC power supply, thus constituting an oxygen pump. Another pair of electrodes is mounted on one of the partition members and connected to a DC power supply, thus constituting a limited-current oxygen sensor. Oxygen is introduced into a space between the partition members at all times by the oxygen pump to maintain the gas, which has been supplied through a gas dispersion member into the space, lean.

8 Claims, 6 Drawing Figures

4,574,627

AIR-FUEL RATIO DETECTOR AND METHOD OF MEASURING AIR-FUEL RATIO

BACKGROUND OF THE INVENTION

1. Field of the Invention

The present invention relates to a detector for detecting an air-fuel ratio, or a ratio of air to fuel in an internal combustion engine or the like, and a method of measuring an air-fuel ratio.

2. Description of the Prior Art

It is the current practice to detect oxygen density in an exhaust gas emitted from an internal combustion engine on an automobile or the like and control the amounts of air and fuel to be supplied to the internal combustion engine based on the detected oxygen density value, thereby reducing harmful components in the exhaust gas.

Air-fuel ratio detectors (oxygen sensors) presently available for internal combustion engines for automobiles for detecting oxygen densities operate on the principle of an oxygen concentration cell. This type of air-fuel ratio detector is capable of detecting a stoichiometric air-fuel ratio ($A/F = 14.6$) because of its characteristics. However, such cannot detect air-fuel ratios in other ranges, that is, in a lean range in which the air-fuel ratio is higher than the stoichiometric air-fuel ratio or in a rich range in which the air-fuel ratio is lower than the stoichiometric air-fuel ratio. When a voltage is applied between gas-permeable thin-film electrodes attached to a solid electrolyte cell permeable to oxygen ions, oxygen ions pass through the cell from the cathode to the anode, and with the passing of the oxygen ions an electric current flows between the electrodes. If the quantity of oxygen ions which are to pass though the cell is limited, then the current is not increased beyond a certain value even when an applied voltage is increased. Utilizing such phenomenon, there has been developed a limited-current oxygen sensor for detecting oxygen densities with a view to detecting air-fuel ratios in the lean range. Since the limited-current oxygen sensor is capable of detecting air-fuel ratios in the lean range only, it is called a "lean sensor", and is almost incapable of detecting air-fuel ratios in the rich range.

While an automobile is running under ordinary conditions, it is preferable that it be driven in the lean range wherein the air-fuel mixture is leaner. When the engine is required to produce a higher power output such as in the case of running up a slope, the automobile is to be preferably driven in the rich range. Therefore, there has been a demand for a detector capable of detecting an air-fuel ratio of from the rich range to the lean range.

SUMMARY OF THE INVENTION

It is an object of the present invention to provide an air-fuel ratio detector capable of detecting, by itself, an air-fuel ratio of from the rich range to the lean range.

Another object of the present invention is to enable an engine to be controlled more efficiently by, for example, burning a lean air-fuel mixture for an economical viewpoint when an automobile is running under ordinary conditions and burning a rich air-fuel mixture for a greater power output than when the automobile is running up a slope.

Still another object of the present invention is to provide a method of continuously measuring air-fuel ratios in a wide range covering the rich to the lean range.

The above objects can be achieved by an air-fuel ratio detector comprising a tubular body, a pair of partition members hermetically engaged on an inner peripheral surface of the tubular body transversely of an axis of the tubular body, at least one of which is composed of a solid electrolyte permeable to oxygen ions, a gas dispersion part which is provided in the tubular body or the other partition member for introducing the gas to be detected and dispersing it into the space by the pair of partition members, a first pair of electrodes mounted on opposite sides of the solid electrolyte and connected to a DC constant-current power supply for introducing oxygen ions into the aforementioned space by permeating the solid electrolyte, and a second pair of electrodes mounted on opposite sides of the electrolyte and connected to an DC constant-voltage power supply which constitutes a lean sensor.

The tubular body may be of various materials, but should preferably be of an inorganic material such as, for example, thermally resistant ceramics.

The tubular body has a closed end having a gas dispersion hole or gas dispersion layer as a gas dispersion part.

The gas dispersion hole may be formed in an ordinary fashion by applying a laser beam to the tubular body formed of ceramics, or by placing strings or other soluble materials in a mass of raw ceramics and then sintering the ceramics mass.

The gas dispersion layer may be formed by joining a ceramic filter to an opening in the tubular body or fabricating a porous ceramic coating on a coarse porous ceramic body with plasma spraying.

The gas dispersion hole or layer may be positioned at a side wall of the tubular body near the closed end thereof. The gas dispersion hole or layer is employed to serve the same purpose as that of the gas dispersion hole or layer in lean sensors.

The tubular body may be in the shape of a cylinder or an angular tube.

When the detector is not used in a high-temperature atmosphere, the solid electrolyte is heated by a heating means in the tubular body. The heating means may comprise a heater in the form of a Nichrome wire coiled around the tubular body, or preferably a heater embedded in the tubular body so that the latter will act as a ceramic heater. The heater is positioned in the vicinity of the solid electrolyte.

The solid electrolyte permeable to oxygen ions may be of the type which is employed in an air-fuel ratio detector or oxygen sensor of the kind described. That is, it may be formed preferably as a flat plate consisting of zirconium oxide added with yttrium oxide.

The electrodes mounted on the surfaces of the solid electrolyte are in the form of gas-permeable thin films formed of platinum in an ordinary manner. The electrodes are provided in two pairs and respectively mounted on opposite surfaces of the plate-like solid electrolyte. The electrodes in each pair are coextensive with each other on opposite surfaces of the solid electrolyte.

One pair of the two pairs of the electrodes is employed as an oxygen pump, and the other pair of electrodes is used as a limited-current oxygen sensor (hereinafter referred to as a "lean sensor"), which is operated by a voltage being applied thereto.

According to conventional lean sensors, their output current is substantially zero at a stoichiometric air-fuel ratio as shown by the solid line A in FIG. 1, and hence only air-fuel ratios in the lean range can be detected for the reason that the oxygen density in the exhaust gas is substantially zero at the stoichiometric air-fuel ratio.

In the air-fuel ratio detector of the present invention, a constant amount of oxygen is supplied by the oxygen pump from atmosphere into the gas to be inspected such as an exhaust gas in a space defined between the dispersion hole (or dispersion layer) and the first solid electrolyte. Therefore, the air-fuel ratio at which the output current from the lean sensor is zero can be shifted into the rich range. In addition, the air-fuel ratio at which the output current from the lean sensor is zero can be varied as desired as shown by the broken line B in FIG. 1 by increasing or reducing the current flowing through the oxygen pump cell. Accordingly, a desired range in which an air-fuel ratio can be detected can be selected.

As will be described hereinafter with respect to embodiments of the invention, the lean sensor may be composed of a separate second solid electrolyte, rather than being constructed with the oxygen pump of the first solid electrolyte. The second solid electrolyte may be disposed at the closed end of the tubular body and the dispersion hole may be formed in the solid electrolyte. The gas to be inspected must be introduced into the space between the first and second solid electrolytes.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 2:
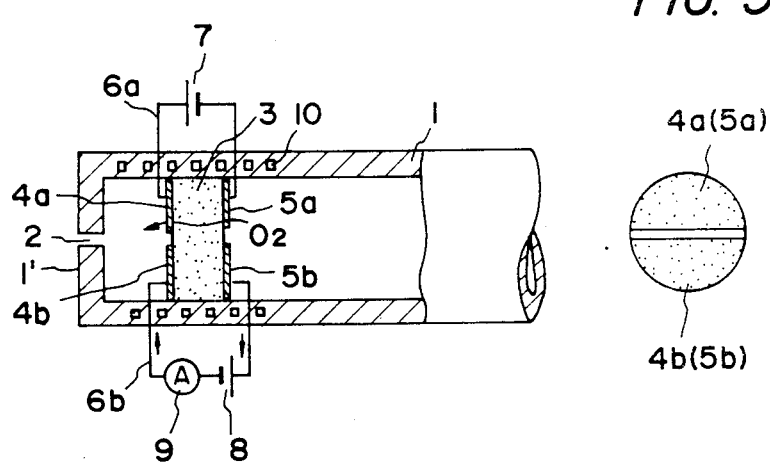
FIG. 2 is a fragmentary cross-sectional view of an air-fuel ratio detector according to a first embodiment of the present invention.

FIG. 2 shows a cross-section of an air-fuel ratio detector according to a first embodiment of the present invention. The air-fuel ratio detector comprises a cylindrical tubular body 1 made of ceramic having a gas dispersion hole 2 defined in a closed end 1' or partition member of the body 1. The cylindrical tubular body 1 accommodates therein a disk-shaped solid electrolyte 3 supporting electrodes 4a, 4b, 5a, 5b thereon and which also acts as a partition member.

Figure 3:
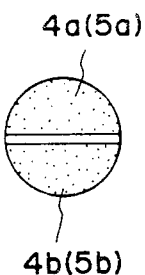
FIG. 3 is a plan view of the electrodes arranged on a solid electrolyte.

The electrodes 4a, 4b, 5a, 5b are of a semicircular shape and attached to opposite surfaces of the solid electrolyte 3, as illustrated in FIG. 3.

The electrodes 4a, 4b disposed on one surface of the solid electrolyte 3 face the gas dispersion hole 2 so that a gas to be inspected such as an exhaust gas is brought into contact with the electrodes 4a, 4b. The electrodes 5a, 5b disposed on the opposite surface of the solid electrolyte 3 are kept in contact with atmosphere. At least the electrodes 4a, 4b which contact the gas should comprise catalytically active electrodes.

As shown in FIG. 2, the electrodes 4a, 5a are paired and connected by lead wires 6a to a DC constant-current power supply 7, thus constituting an oxygen pump. The other pair of electrodes 4b, 5b are also connected by lead wire 6b to a DC constant-voltage power supply 8 and a current measuring device 9, thus constituting a lean sensor.

As illustrated in FIG. 2, a heater 10 is disposed in the cylindrical tubular body 1 as an ordinary ceramic heater. The heater 10 is connected by lead wires (not shown) to a power supply. When necessary to meet the requirements deriving from the characteristic of the detector, the heater 10 is energized to heat the air-fuel ratio detector. For example, the heater 10 is energized when the detector does not reach a required operating temperature at the time of detecting an exhaust gas of low temperature resulting from combustion of a lean air-fuel mixture.

The air-fuel ratio detector of the foregoing construction is therefore a combination of a conventional pin hole-type lean sensor and an oxygen sensor.

Figure 1:
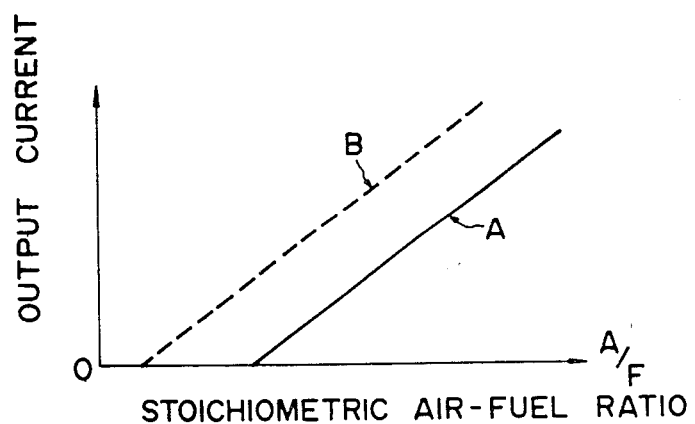
FIG. 1 is a graph showing the relationship between a stoichiometric air-fuel ratio and an output electric current.

According to the air-fuel ratio detector of the present invention, a constant amount of oxygen flows at all times through the electrode 5a to the electrode 4a as an oxygen pump, and therefore the gas to be inspected which has entered into the space through the gas dispersion hole 2 is converted into a lean condition even if it was originally in a rich condition. Thus the lean sensor can detect the air-fuel ratio of the gas kept in the space between the gas dispersion hole 2 and the solid electrolyte 3. The air-fuel ratio detected by the air-fuel ratio detector of the present invention is indicated by the broken line B in FIG. 1. With the amount of oxygen to be supplied into the gas being predetermined, a true air-fuel ratio of the gas can be determined by correcting the difference between the air-fuel ratio B and an air-fuel ratio detected by a conventional lean sensor and indicated by the solid line A in FIG. 1.

Other embodiments of the air-fuel ratio detectors according to the present invention will be described with reference to FIGS. 4 through 6.

Figure 4:
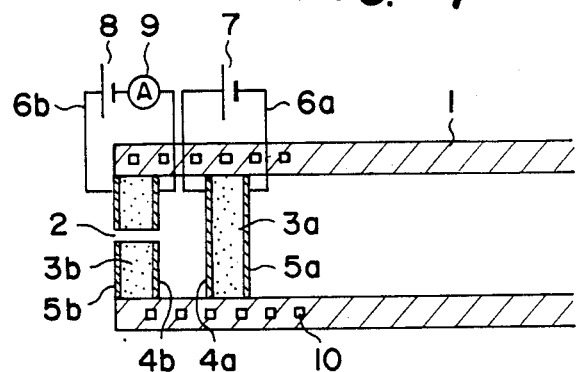
FIGS. 4 through 6 are fragmentary cross-sectional views of air-fuel ratio detectors according to other embodiments of the present invention.

According to a second embodiment shown in FIG. 4, an air-fuel ratio detector has two solid electrolytes 3a, 3b spaced from each other, the solid electrolyte 3a with electrodes 4a and 5a serving as an oxygen pump or partition member and the solid electrolyte 3b with electrodes 4b and 5b serving as a lean sensor. The solid electrolyte 3b also serves as a closed end or partition member of a cylindrical tubular body 1 and has a gas dispersion hole 2 serving as a gas dispersion part.

Figure 5:
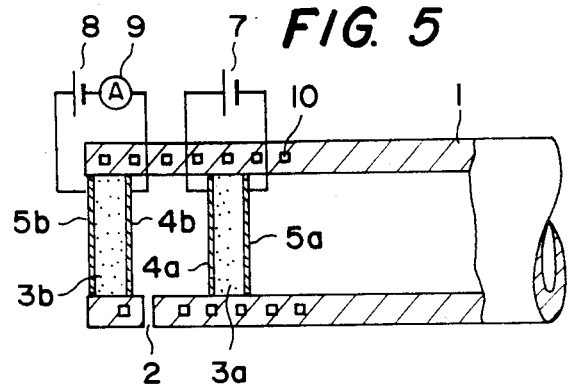

FIG. 5 illustrates an air-fuel ratio sensor of a third embodiment. The air-fuel ratio sensor includes a cylindrical tubular body 1 having a gas dispersion hole 2 defined in a side wall thereof.

Figure 6:
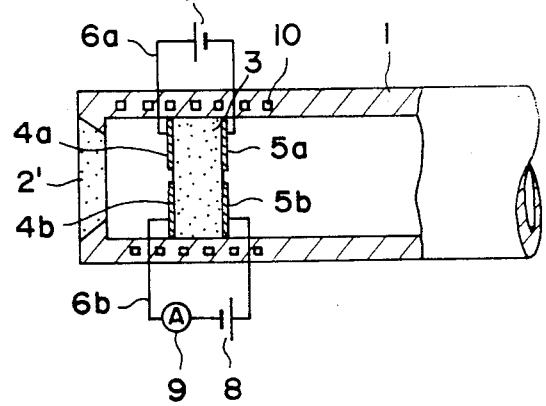

FIG. 6 shows an air-fuel ratio detector according to a fourth embodiment. The air-fuel ratio detector has a gas dispersion layer 2' disposed in an end of a cylindrical tubular body 1.

Although certain preferred embodiments have been shown and described, it should be understood that many changes and modifications may be made therein without departing from the scope of the appended claims.

What is claimed as new and desired to be secured by Letters Patent of the United States is:

1. An air-fuel ratio detector for detecting oxygen density in exhaust gas emitted from an engine, comprising:
   a DC constant-current supply and constant voltage supply;
   a tubular body;
   first and second partition members hermetically contacting an inner peripheral surface of said tubular body transversely of an axis of said tubular body, wherein at least said first partition member further comprises a solid electrolyte permeable to oxygen ions;
   gas dispersion means communicating a space between said partition members with said exhaust gases for introducing gas to be detected and dispersing said gas into a space defined between said first and second partition members;
   a first pair of electrodes separately mounted on opposite sides of said first partition member and connected to said DC constant-current supply for introducing oxygen ions by permeating into said space through said solid electrolyte;
   a second pair of electrodes separately mounted on opposite sides of one of said first and second partition members and connected to said DC constant-voltage supply, and
   means for measuring an air-fuel ratio in said gas based on a current generated between said second pair of electrodes.

2. An air-fuel ratio detector according to claim 1, wherein said second partition member further comprises an end portion of said tubular body, said gas dispersion means being located in said end portion and said second partition member being disposed in said tubular body to divide said tubular body into a closed-end section and an open-end section defining said space and wherein one of said first and second pair of electrodes and said DC constant-current supply connected thereto in combination further comprises an oxygen pump, and the other pair and the DC constant-voltage supply connected thereto in combination further comprises a limited-current oxygen sensor.

3. An air-fuel ratio detector according to claim 1, wherein said gas dispersion means further comprises a gas dispersion layer located in said second partition member.

4. An air-fuel ratio detector for detecting oxygen density in exhaust gas emitted from an engine, comprising:
   a DC constant-current supply and constant voltage power supply;
   a tubular body;
   first and second partition members forming a space therebetween and hermetically contacting an inner peripheral surface of said tubular body, wherein said first and second partition members each further comprises a solid electrolyte and divide the tubular body into a closed end section defining said space and an open-end section;
   a first pair of electrodes mounted on opposite sides of said solid electrolyte of said first partition member and connected to said DC constant-voltage supply for introducing oxygen ions by permeating into the aforementioned space through said solid electrolyte;
   a second pair of electrodes mounted on opposite sides of said solid electrolyte of said second partition member and connected to said DC constant-current supply; and
   means for measuring an air-fuel ratio in said gas based on a current generated between said second pair of electrodes.

5. An air-fuel ratio detector according to claim 4, including gas dispersion means comprising a gas dispersion hole defined in said second partition member.

6. An air-fuel ratio detector for detecting oxygen density in exhaust gas emitted from an engine, comprising:
   a DC constant-current supply and constant voltage supply;
   a tubular body;
   first and second partition members hermetically contacting an inner peripheral surface of said tubular body transversely of an axis of said tubular body wherein said first and second partition members each further comprises a solid electrolyte permeable to oxygen ions;
   gas dispersion means formed in said tubular portion for introducing the gas to be detected and dispersing said gas into a space defined between said first and second partition members;
   a first pair of electrodes mounted on said first partition means and connected to said DC constant-current supply for introducing oxygen ions by permeating into said space through said solid electrolyte of said first partition;
   a second pair of electrodes mounted on opposite sides of said second partition member and connected to said DC constant-voltage supply; and
   means for measuring an air-fuel ratio in said gas based on a current generated between said second pair of electrodes.

7. A method of measuring an air-fuel ratio for detecting oxygen density in an exhaust gas emitted from an engine, which comprises:
   introducing oxygen into a closed space into which said exhaust gas to be inspected flows by passing a DC current between a pair of electrodes separately mounted on opposite sides of a solid electrolyte permeable to oxygen ions and which constitutes a portion of a partition defining said space;
   applying a DC voltage between a second pair of electrodes separately mounted on opposite sides of another portion of said partition; and
   measuring an air-fuel ratio in said second gas based on a current generated between said pair of electrodes.

8. A method of measuring an air-fuel ratio for detecting oxygen density in an exhaust gas emitted from an engine, which comprises:
   introducing oxygen into a closed space into which a gas to be inspected flows by passing a DC current between a first pair of electrodes separately mounted on opposite sides of a first solid electrolyte permeable to oxygen ions and which constitutes a portion of a partition defining said space;
   applying a DC voltage between a second pair of electrodes separately mounted on opposite sides of a second solid electrolyte; and
   measuring an air-fuel ratio in said gas based on a current generated between said second pair of electrodes.

* * * * *